United States Patent
Nakanishi et al.

(10) Patent No.: US 6,448,027 B1
(45) Date of Patent: Sep. 10, 2002

(54) METHOD FOR SPECIFIC MEASUREMENT OF ACID PHOSPHATASE DERIVED FROM OSTEOCLASTS

(75) Inventors: Mamoru Nakanishi, Joyo; Kagehiro Uchida, Osaka, both of (JP)

(73) Assignee: FALCO biosystems Ltd., Kyoto (JP)

( * ) Notice: Subject to any disclaimer, the term of this patent is extended or adjusted under 35 U.S.C. 154(b) by 0 days.

(21) Appl. No.: 09/604,279

(22) Filed: Jun. 26, 2000

(30) Foreign Application Priority Data

Dec. 15, 1999 (JP) ............................................. 11-355943
Jan. 21, 2000 (JP) ........................................ 2000-012983

(51) Int. Cl.⁷ ............................. C12Q 1/42; C12Q 1/34; C12Q 1/00
(52) U.S. Cl. ................................ 435/21; 435/18; 435/4
(58) Field of Search .................................. 435/21, 18, 4

(56) References Cited

U.S. PATENT DOCUMENTS 4,652,555 A * 3/1987 Goulay et al.
6,248,544 B1 * 6/2001 Halleen et al. ............... 435/7.4

OTHER PUBLICATIONS

Nakanishi et al. Development of a Method for Measurement of Band Tracp Activity. Nippon Kotsu–Taisha Gakkai Zasshi, vol. 17, No. 2, pp. 250, 1999.

*Development of a Kinetic Assay for Band 5b Tartrate–resistant Acid Phosphatase Activity in Serum*; Clinical Chemistry 46:4; 469–473 (2000), by Mamoru Nakanishi; Kousei Yoh, Toshihide Miura; Tatsuya Ohasi; Shiba Kumar Rai; and Kagehiro Uchida.

*Improved method for measuring tartrate–resistant acid phosphatase acitivity in serum*; Clinical Chemistry, 44:2; 221–225 (1998), by Mamoru Nakanishi; Kousei Yoh, Kagehiro Uchida; Souji Maruo and Akira Matsuoka.

* cited by examiner

Primary Examiner—Ralph Gitomer
Assistant Examiner—Mahreen Chaudhry
(74) Attorney, Agent, or Firm—Donald R. Studebaker; Nixon Peabody LLP (57) ABSTRACT

A method for measuring activity of osteoclast-derived acid phosphatase located at Band 5*b* of Band 5 in polyacrylamide gel electrophoresis of a sample which is characterized by using an inhibitor to acid phosphatases located at Band 5 other than Band 5*b*; and a composition and a kit for using in the method.

16 Claims, 5 Drawing Sheets

METHOD FOR SPECIFIC MEASUREMENT OF ACID PHOSPHATASE DERIVED FROM OSTEOCLASTS

FIELD OF THE INVENTION

The present invention relates to a method for measuring activity of osteoclast-derived acid phosphatase which is specific for bone metabolism. According to the present invention, the measurement of osteoclast-derived acid phosphatase activity can be carried out easily and specifically. And, the method is very useful measurement for clinical tests in the field of medical treatment and clinical assessment.

BACKGROUND OF THE INVENTION

Acid phosphatases are enzymes having acidic optimal pH, and hydrolyzing organic mono-phosphoric esters. Various kinds of the enzymes such as prostate-derived acid phosphatase, osteoclast-derived acid phosphatase, erythrocyte-derived acid phosphatase and platelet-derived acid phosphatase have been known and the enzymes can be separated into 6 bands of 0 to 5 by electrophoresis. Tartrate-resistant acid phosphatases in serum whose enzyme activities are not inhibited by addition of a tartrate are present at Band 5 and almost all of them are thought to be osteoclast-derived acid phosphatase. Then, their measurement is thought to be useful as an indicator for evaluating functions of osteoclasts and is expected to be a marker for bone resorption [(Hone-taisha (Bone Metabolism) Marker, Hitoo, Fukunaga, et al., Medical Review, 1995).

Generally, for measuring tartrate-resistant acid phosphatases in a sample by enzyme activity measurement, their activity is determined by colorimetry of a product (such as alcohol and phenols) produced by an enzyme reaction using a phosphoric ester as a synthetic substrate in the presence of a tartrate. Upon the reaction, the tartrate inhibits mainly prostate-derived acid phosphatase which co-exists in the sample. Therefore, tartrate-resistant acid phosphatase activity is determined as an indicator of osteoclast-derived acid phosphatase activity by measuring the remaining acid phosphatase activity using the substrate. In a method known to be more improved and specific measurement of osteoclast-derived acid phosphatase activity, serum is diluted 5 times, the resultant solution is incubated at 37° C. for 1 hour, and then the remaining tartrate-resistant acid phosphatase activity is measured using p-nitrophenyl phosphoric acid as the substrate in the presence of a tartrate (Nichi-dai ishi, Vol. 49, 904–911, 1990: Clin. Chem., Vol. 3, 458–462, 1987).

The above methods, wherein tartrate-resistant acid phosphatase activity is measured as an indicator of osteoclast-derived acid phosphatase, have problems in specificity, sensitivity, complexity of measurement and measuring time. In a sample, there are erythrocyte-derived acid phosphatase and platelet-derived acid phosphatase as tartrate-resistant acid phosphatase in addition to osteoclast-derived acid phosphatase. That is, when hemolysis occurs by collection of a sample, erythrocyte-derived acid phosphatase is contained in the sample. Also, when serum is used as a sample, platelet-derived acid phosphatase is contained in the sample by destruction of platelets during blood coagulation in preparation of the serum. Thus, it cannot be said that the above measurement of tartrate-resistant acid phosphatase activity determines osteoclast-derived acid phosphatase activity specifically.

For a method for measuring osteoclast-derived acid phosphatase without influence of erythrocyte and platelet-derived acid phosphatases, the present inventors previously found that there is a difference in resistance to a fluoride between erythrocyte- and platelet-derived acid phosphatases and osteoclast-derived acid phosphatase, and reported a method for determination of osteoclast-derived acid phosphatase activity by measuring both tartrate-resistant acid phosphatase activity and tartrate-resistant fluoride-resistant acid phosphatase activity, and then calculating the difference between them (JP 10-337198 A).

Tartrate-resistant acid phosphatases in serum are located at a fifth band from the starting point by electrophoresis and are called Band 5 tartrate-resistant acid phosphatase (hereinafter, sometimes, referred to as "acid phosphatase located at Band 5"). Band 5 tartrate-resistant acid phosphatase can be separated into a component located at Band 5a and has many binding glycoproteins and another component located at Band 5b and has less binding glycoproteins (hereinafter, sometimes, referred to as "Band 5a tartrate-resistant acid phosphatase" or "acid phosphatase located at Band 5a" and "Band 5b tartrate-resistant acid phosphatase" or "acid phosphatase located at Band 5b", respectively.). Production processes and functional mechanisms in a living body of Band 5a and Band 5b tartrate-resistant acid phosphatases are not yet elucidated. However, Band 5b tartrate-resistant acid phosphatase varies with bone metabolism, while Band 5a tartrate-resistant acid phosphatase dose not vary. In view of this, Band 5b tartrate-resistant acid phosphatase is considered to be very concerned with bone metabolism and to be osteoclast-derived acid phosphatase (Lam, K. W., Lai, L., and Yam, L. T., Clin. Chem. , 1978, 24, 309–312). Therefor, a simple method for specific measurement of Band 5b tartrate-resistant acid phosphatase has been desired.

In the method for measuring osteoclast-derived acid phosphatase activity reported in the above JP 10-337198 A, tartrate-resistant fluoride-sensitive acid phosphatase is regarded as osteoclast-derived acid phosphatase. Then, the method cannot differentiate acid phosphatase activity of Band 5a acid phosphatase having many binding glycoproteins from that of Band 5b acid phosphatase having less binding glycoproteins, and cannot measure specifically the activity of acid phosphatase which is specific for bone metabolism.

OBJECTS OF THE INVENTION

In view of these circumstances, an object of the present invention is to provide a simple, economical and clinically available method for specific measurement of activity of osteoclast-derived acid phosphatase which is specific for bone metabolism and located at Band 5b, and a kit for using in the method.

SUMMARY OF THE INVENTION

The present inventors have studied intensively to solve the above problems in the prior art. As a result, it has been found that the activities between Band 5a and Band 5b tartrate-resistant acid phosphatases can be differentiated from each other by treating tartrate-resistant acid phosphatase with an acid mucopolysaccharide. Thus, the present invention has been completed.

That is, according to the present invention, there is provided a method for measuring activity of osteoclast-derived acid phosphatase located at Band 5b of Band 5 in polyacrylamide gel electrophoresis of a sample which comprises using an inhibitor to acid phosphatases located at Band 5 other than Band 5b.

More particular, the present invention provides a method for measuring activity of osteoclast-derived acid phosphatase located at Band 5b of Band 5 in polyacrylamide gel electrophoresis of a sample which comprises:

(i) treating acid phosphatases in the sample with a substrate for the measurement of acid phosphatase activity in the presence of an inhibitor to prostate-derived acid phosphatase and an inhibitor to acid phosphatases located at Band 5 other than Band 5b to measure acid phosphatase activity (hereinafter, sometimes, referred to as "measurement 1");

(ii) independently of (i), treating acid phosphatases in the sample with a substrate for the measurement of acid phosphatase activity in the presence of an inhibitor to prostate-derived acid phosphatase and an inhibitor to acid phosphatases located at Band 5 to measure acid phosphatase activity (hereinafter, sometimes, referred to as "measurement 2"); and then, (iii) subtracting the activity of the above (ii) from the activity of the above (i) to obtain the activity of osteoclast-derived acid phosphatase located at Band 5b.

The present invention also provides a composition and a kit for using in these methods.

DETAILED DESCRIPTION OF THE INVENTION

Typical examples of the sample to be used in the present invention include human blood, serum, plasma and the like.

According to the method of the present invention, activities of osteoclast-derived acid phosphatase located at Band 5b and acid phosphatases located at Band 5 other than Band 5b can be measured separately by using the inhibitor to acid phosphatases located at Band 5 other than Band 5b in polyacrylamide gel electrophoresis.

In measurement 1 of the present method, prostate-derived acid phosphatase in the sample is inhibited, while acid phosphatases located at Band 5 as well as erythrocyte-derived acid phosphatase and platelet-derived acid phosphatase are not inhibited in the presence of the inhibitor to prostate-derived acid phosphatase. In the presence of the inhibitor to acid phosphatases located at Band 5 other than Band 5b, (tartrate-resistant fluoride-sensitive) acid phosphatases located at Band 5 other than Band 5b are inhibited, while osteoclast-derived (tartrate-resistant fluoride-sensitive) acid phosphatase, erythrocyte-derived acid phosphatase and platelet-derived acid phosphatase are not inhibited. That is, in measurement 1, the sum of osteoclast-derived acid phosphatase located at Band 5b, erythrocyte-derived acid phosphatase and platelet-derived acid phosphatase corresponds to the activity. On the other hand, in measurement 2, prostate-derived acid phosphatase is inhibited, while acid phosphatases located at Band 5, erythrocyte-derived acid phosphatase and platelet-derived acid phosphatase are not inhibited in the presence of the inhibitor to prostate-derived acid phosphatase. In the presence of the inhibitor to all the acid phosphatases located at Band 5, (tartrate-resistant fluoride-sensitive) acid phosphatases are inhibited, while erythrocyte-derived acid phosphatase and platelet-derived acid phosphatase are not inhibited. That is, in measurement 2, the sum of erythrocyte-derived acid phosphatase and platelet-derived acid phosphatase corresponds to the activity. As a result, the activity of osteoclast-derived acid phosphatase located at Band 5b can be specifically measured by subtracting the value of measurement 2 from the value of measurement 1. When the inhibitor to acid phosphatases located at Band 5 other than Band 5b is added further in measurement 2, the same result is obtained.

The inhibitor to acid phosphatases located at Band 5 other than Band 5b used in the present invention is not limited to a specific one as far as it inhibits acid phosphatases located at Band 5 other than Band 5b and does not inhibit osteoclast-derived acid phosphatase located at Band 5b. Examples of such material (hereinafter, sometimes merely referred to as "inhibitor") include acid mucopolysaccharides such as hyaluronic acid, chondroitins, heparin, heparan sulfate, keratan sulfate and the like, and heparin is preferred. Heparin can be used as its salt with sodium, lithium, calcium and the like, preferably heparin sodium is used. Upon reacted with a substrate, the preferred inhibitor concentration is above 100 IU/L (the same result is obtained up to its saturated amount), more preferably 1,000 IU/L to 200,000 IU/L.

Examples of the inhibitors of prostate-derived acid phosphatase used in the present invention include tartaric acid, and L-(+)-tartaric acid or its salts such as sodium salt and potassium salt are preferred. When acid phosphatase is treated with the substrate in the presence of tartaric acid, the tartaric acid concentration is preferably 5 to 500 mM, more preferably 20 to 200 mM.

The inhibitor to acid phosphatases located at Band 5 used in the present invention is not limited to a specific one as far as it dose not inhibit erythrocyte- and platelet-derived acid phosphatases and inhibits all the acid phosphatases located at Band 5. Examples of such inhibitor are fluorides and sodium fluoride, potassium fluoride and the like are preferred. When acid phosphatase is treated with the substrate in the presence of a fluoride, preferred fluoride concentration is 5 to 500 mM, more preferred 20 to 200 mM.

The substrate for the measurement of acid phosphatase activity used in the present invention is not limited to a specific one as far as it can react with acid phosphatase to measure acid phosphatase, in particular osteoclast-derived acid phosphatase located at Band 5b. Similarly, the measurement method is not limited to a specific one as far as it can measure acid phosphatase, in particular osteoclast-derived acid phosphatase located at Band 5b, and rate assay, end point assay or the like can be used. Examples of the substrate for the rate assay include a-naphthyl phosphoric acid and its salt, 2,6-dichloro-4-nitrophenyl phosphoric acid and its salt, 2-chloro-4-nitrophenyl phosphoric acid and its salt, 2,6-dichloro-4-acetylphenyl phosphoric acid and its salt and the like. Examples of the substrate for the end point assay include phenyl phosphoric acid, p-nitrophenyl phosphoric acid and the like.

Preferred substrate concentration for the reaction is 5 to 10 times as much as Km of each substrate against acid phosphatase. In the present invention, for measuring acid phosphatase activity in the sample, the amount of alcohol or phenol formed can be measured by measuring change in absorbance at appreciate wavelength using a spectrophotometer or a automatic analyzer. In this case, acid phosphatase activity is measured by using the following formula in rate assay.

Activity=[(amount of change in absorbance per unit time in enzyme reaction−amount of change in absorbance in blank)× liquid amount on enzyme reaction]÷[sample amount×molar absorbance coefficient×cell optical path length]

(wherein, "amount of absorbance change in blank" means a value obtained by the similar procedure with "amount of change in absorbance per unit time in enzyme reaction" except for using physical saline or purified water instead of the sample).

In the rate assay using the automatic analyzer, the measurement can be completed within very short time, such as 10 to 20 minutes. The amount of the reaction mixture on the enzyme reaction is preferably not less than 5 times, more preferably 10 to 50 times as much as the amount of the sample used. When the amount of the reaction mixture is less than 5 times, osteoclast-derived acid phosphatase located at Band 5b and tartrate-resistant fluoride-sensitive acid phosphatase can hardly be measured exactly due to influence of inhibiting material(s) in the sample. On the other hand, when the amount of the reaction mixture is too much, sometimes, osteoclast-derived acid phosphatase located at Band 5b can not be measured specifically due to lowering of the measurement sensitivity due to too much substrate.

If necessary, surfactants such as Triton x-100, alcohols, proteins such as albumin can be contained in the enzyme reaction. In the enzyme reaction, acidic region of pH 4 to 7 is preferred and pH 5.4 to 7.0 is more preferred. Then, buffer agents such as citric acid and its salts, acetic acid and its salts, MES, MOPSO, Bis-Tris and the like may be used.

For the method for measuring osteoclast-derived acid phosphatase located at Band 5b of Band 5 in polyacrylamide gel electrophoresis of the present invention, a composition comprising an inhibitor to acid phosphatases located at Band 5 other than Band 5b may be used. For example, a kit comprising (a) a composition comprising an inhibitor to acid phosphatases located at Band 5 other than Band 5b, (b) a composition comprising an inhibitor to prostate-derived acid phosphatase, (c) a composition comprising an inhibitor to acid phosphatases located at Band 5, and, (d) a composition comprising a substrate for measurement of acid phosphatase activity, may be used. This kit may contain the respective compositions of (a) to (d) separately. Further, it may contain the compositions premixed with more than one composition(s), for example, may contain the mixture of the composition of (a) and the composition of (b), or the composition of (b) and the composition of (c).

Among these, it is preferred to use a kit comprising (i) a composition comprising an inhibitor to prostate-derived acid phosphatase and an inhibitor to acid phosphatases located at Band 5 other than Band 5b, (ii) a composition comprising an inhibitor to prostate-derived acid phosphatase and an inhibitor to acid phosphatases located at Band 5, (iii) a composition comprising a substrate for measurement of acid phosphatase activity. To (ii) may be added the inhibitor to the acid phosphatases located at Band 5 other than Band 5b optionally.

These kits can be applied to an automatic analyzer of 2-compositions system. The compositions may optionally contain surfactants such as Triton x-100, alcohols, salts such as sodium chloride and proteins such as albumin. In the enzyme reaction, acidic region of pH 4 to 7 is preferred and pH 5.4 to 7.0 is more preferred. Therefor, buffer agents such as citric acid and its salts, acetic acid and its salts, MES, MOPSO, Bis-Tris and the like may be used.

In the kit, first, the sample and the composition comprising the inhibitor to prostate-derived acid phosphatase and the inhibitor to acid phosphatases located at Band 5 other than Band 5b are mixed to inhibit prostate-derived acid phosphatase and the acid phosphatases located at Band 5 other than Band 5b, and then to the resultant mixture are added the composition of the substrate to measure remaining acid phosphatase activity (measurement 1). Independently, the sample and the composition comprising the inhibitor to prostate-derived acid phosphatase and the inhibitor to the acid phosphatases located at Band 5 are mixed to inhibit prostate-derived acid phosphatase and the acid phosphatases located at Band 5, and then to the resultant mixture are added the composition of the substrate to measure remaining acid phosphatase activity (measurement 2). The activity of measurement 2 can be subtracted from the activity of measurement 1 to obtain activity of osteoclast-derived acid phosphatase located at Band 5b in the sample. In measurement 2, the same result is also obtained by adding the inhibitor to acid phosphatases located at Band 5 other than Band 5b.

The following Examples further illustrate the present invention in detail but are not to be construed to limit the scope thereof.

EXAMPLES

General Method of the Activity Measurement (1) Formulation of Compositions (a) A Composition Comprising Tartaric Acid and Heparin (Reaction Buffer Solution 1)

150 mM MOPOS (2-hydroxy-3-moropholino-propane-sufonic acid, good buffer solution; Dojin Chemical Institute)

60 mM sodium L(+)-tartrate (Shigma Chemical Co.)

0.5% bovine albumin (Shigma Chemical Co.)

0.05% sodium heparin (Shigma Chemical Co.)

0.1% TritonX-100 (Wako Pure Chemical Co.)

pH 6.6 (25° C.)

(b) A composition comprising tartaric acid, heparin and fluoride (reaction buffer solution 2)

150 mM MOPOS (good buffer solution; Dojin Chemical Institute)

60 mM sodium L(+)-tartrate (Shigma Chemical Co.)

0.5% bovine albumin (Shigma Chemical Co.)

0.05% sodium heparin (Shigma Chemical Co.)

45 mM sodium fluoride (Wako Pure Chemical Co.)

0.1% TritonX-100 (Wako Pure Chemical Co.) pH 6.6 (25° C.)

(c) A Substrate Solution 50 mM Tris (Wako Pure Chemical Co.)

45 mM DCAPP (2,6-dichloro-4-acetylphenyl phosphate, Nitto Boseki Co. Ltd.)

pH 4.0 (25° C.)

(2) Measurement (an Example Using Conventional Automatic Analyzer, Cobas® Fara, Baxter Ltd.)

To a cuvette is added 150 µl of reaction buffer solution 1 or reaction buffer solution 2 and, after 20 seconds, 15 µl of sample (serum) is added. The mixture is incubated at 37° C. for 5 minutes and then 60 µl of the substrate solution is added to start the enzyme reaction (the reaction mixture is 15 times as much as the amount of the sample (=(150 µl+15 µl+60 µl)/15 µl). The change in absorbance at 340 nm is monitored at 20 seconds intervals for 5 minutes. The amount of change in absorbance per one minute (the amount of change in absorbance in the enzyme reaction per unit time) is obtained from a linear part of the change in absorbance. The amount of change in absorbance per one minute in blank is obtained by the same procedure as the above except for adding physical saline or purified water instead of the sample.

The activity of osteoclast-derived acid phosphatase located at Band 5b is obtained by subtracting the activity value obtained by using the composition comprising tartaric acid, heparin and fluoride of the reaction buffer solution 2 from the activity value obtained by using the composition comprising tartaric acid and the inhibitor to acid phosphatases located at Band 5 other than Band 5b (in Examples, heparin is used) of the reaction buffer solution 1. The time required for measuring the activity of osteoclast-derived acid phosphatase located at Band 5b for one sample is about 10 minutes. The concentration, formulation, amount and the like of the above composition are adjusted according to a particular kind of automatic analyzer and measurement (kind and concentration of the substrate and the like) used.

(3) Calculation

Acid phosphatase activity can be obtained by assigning the amount of change in absorbance obtained in the above procedure to the following calculating equation.

Activity (U/L)=[(amount of change in absorbance per unit time in enzyme reaction−amount of change in absorbance in blank)× liquid amount on enzyme reaction×$10^6$]÷[sample amount×molar absorbance coefficient×cell optical path length]

(4) Assigning formulation is shown below.

Activity (U/L)=[($\Delta$E/min sample−$\Delta$E/min blank)×0.225×$10^6$]/ (0.015×21,500×0.9)

wherein;

$\Delta$E/min sample: the amount of change in absorbance per one minute in enzyme reaction $\Delta$E/min blank: the amount of change in absorbance per one minute in blank 0.225: liquid amount on enzyme reaction (ml)

0.015: amount of the sample (ml)

21,500: molar absorbance coefficient (1/mol·cm)

0.9: optical path length (cm).

(3) Serum Sample

Blood samples collected from 516 healthy subjects aged 5 to 79 years (210 males and 306 females) were coagulated at room temperature for 2 to 4 hours and centrifuged at 1,000×g at room temperature for 10 minutes. Serum thus separated was transferred into 1.5 ml tubes and stored at −80° C. until use.

(4) Electrophoresis

Acid phosphatase isoenzymes are analyzed by electrophoresis on an acidic polyacrylamide gel. After the electrophoresis, the gel were washed with acetate buffer (0.1 mol/l, pH 5.2) and stained with a-naphthyl phosphate and Fast Garnet GBC.

In the following Examples, all results are expressed as mean±SD. Statistical significance was evaluated by Student's t-test.

EXAMPLE 1

Separation of Band 5a and Band 5b tartrate-resistant acid phosphatase by cation exchange chromatography Using CM-Sepharose, Band 5a and Band 5b tartrate-resistant acid phosphatase were separated and collected.

The CM-Sepharose was packed into glass tubing (0.9 cm i.d.; length, 60 cm) and washed with acetate buffer (10 mmol/L, pH 5.0). The serum sample (children's serum, 5 ml) was adjusted to pH 5.0 by adding acetic acid and the coagulated proteins were removed by centrifugation at 20,000×g for 15 minutes. The supernatant fraction was passed through the column at 0.5 ml/minute. The enzyme, which was retained on the column, was then eluted with a liner gradient of sodium chloride: 0 to 1 mol/L in elution buffer (299 ml, acetate buffer, 10 mmol/L, pH 5.0). The fractionated serum was subjected to the method described in the above general method to measure tartrate-resistant fluoride-sensitive acid phosphatase activity (the value obtained by subtracting the value obtained with measurement solution 2 from the value obtained with measurement solution 1). Acid phosphatase activity was measured similarly by using measurement solution added polybrene which was antagonist of heparin instead of heparin.

Figure 1:
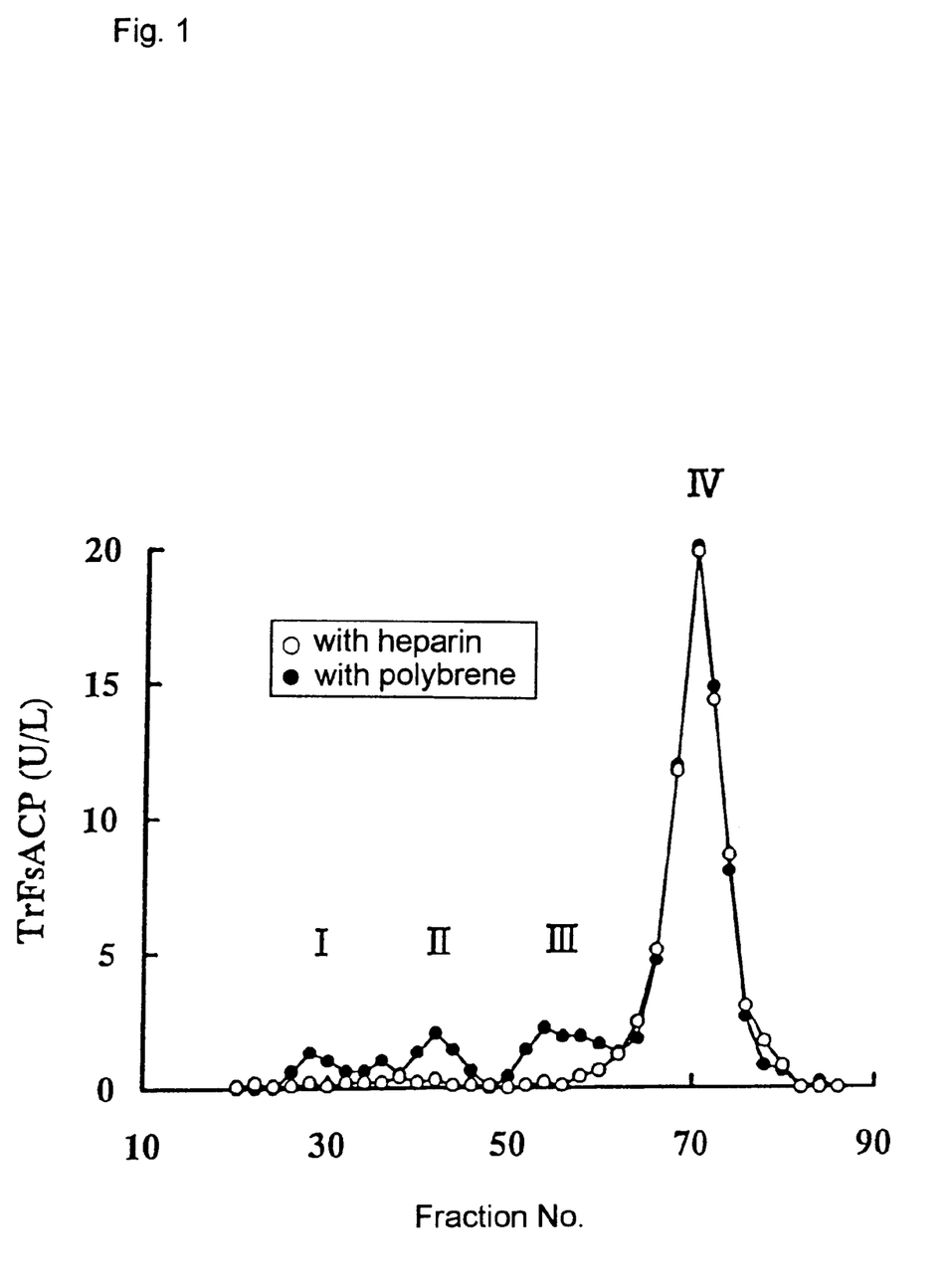
FIG. 1 illustrates the CM-Sepharose chromatographic pattern of serum tartrate-resistant fluoride-sensitive acid phosphatase (TrFsACP).
Figure 2:
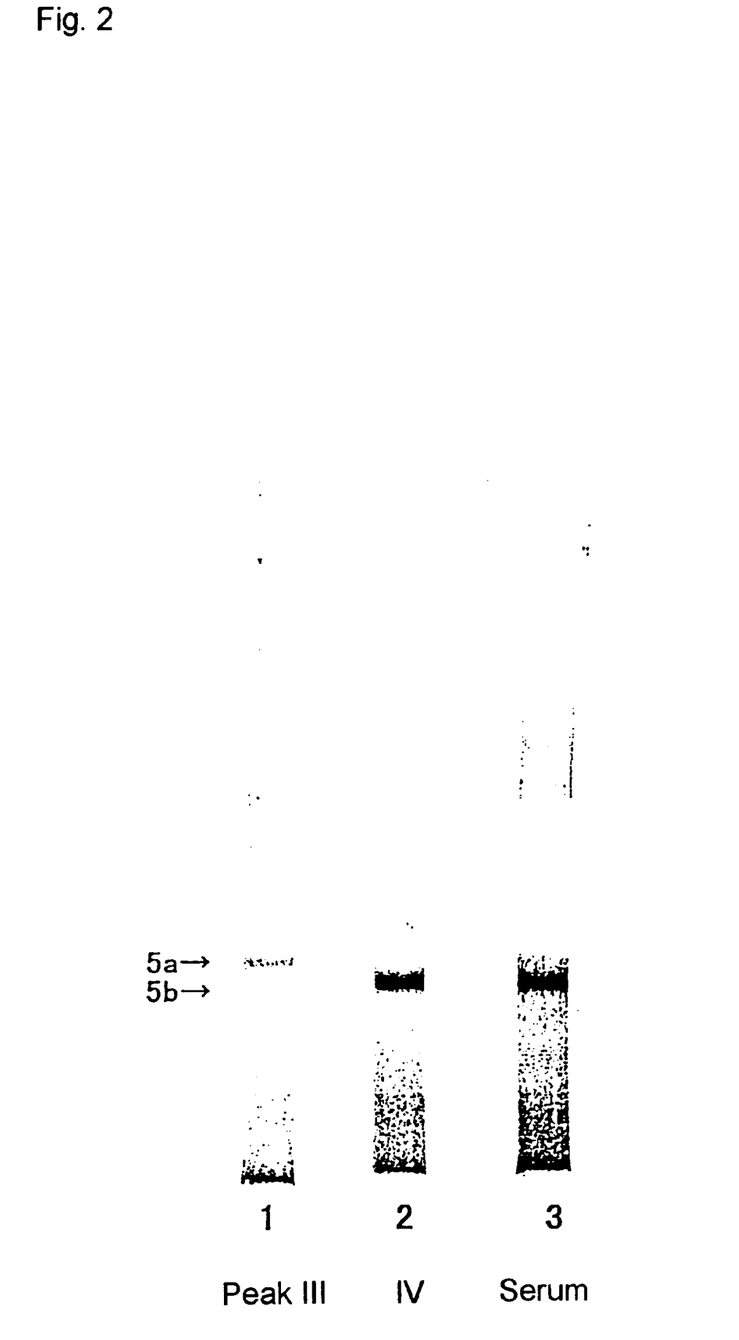
FIG. 2 illustrates the result of electrophoresis of peaks III and IV of tartrate-resistant fluoride-sensitive acid phosphatase (TrFsACP) on polyacrylamide gel. Lane 1, Lane 2 and Lane 3 illustrate peak III, peak IV and children's serum, respectively.

The measurement result is shown in FIG. 1. When polybrene was added to the reaction buffer, at least four peaks of tartrate-resistant fluoride-sensitive acid phosphatase activity were observed (FIG. 1, I, II, III and IV). But only one peak (IV) was observed when heparin was added to the reaction buffer. As a result of polyacrylamide gel electrophoresis of these peaks, it was shown that the peak III and IV were Band 5a and 5b, respectively (FIG. 2).

From the results, it is found that heparin inhibits tartrate-resistant fluoride-sensitive acid phosphatases other than Band 5b. Tartrate-resistant fluoride-sensitive acid phosphatase which is inhibited by heparin appear to be acid phosphatases located at Band 5a and other unknown phosphatase(s).

These fractions containing peak III and IV were used as Band 5a and Band 5b tartrate-resistant acid phosphatase, respectively, in the following Examples.

EXAMPLE 2

Effect of heparin on Band 5a and 5b tartrate-resistant acid phosphatase and bone extract Band 5a and 5b tartrate-resistant acid phosphatases prepared in Example 1 were used.

Bone extract was prepared according to the method described in Nakanishi, M., Yoh, K., Uchida, K., Maruo, S., Matuoka, A., Clin. Chem., 1998, 44, 221–225. Bovine tibia after removal of soft tissue was cut into small cubes. The marrow and blood were removed, pulverized and homogenized in a solution containing Triton x-100, potassium chloride, phenylmethylsulfonyl fluoride, benzamidine and aminocaproic acid. The extract was collected by centrifugation at 10,000×g for 20 minutes at 4° C. and stored at −80° C. until use.

Figure 3:
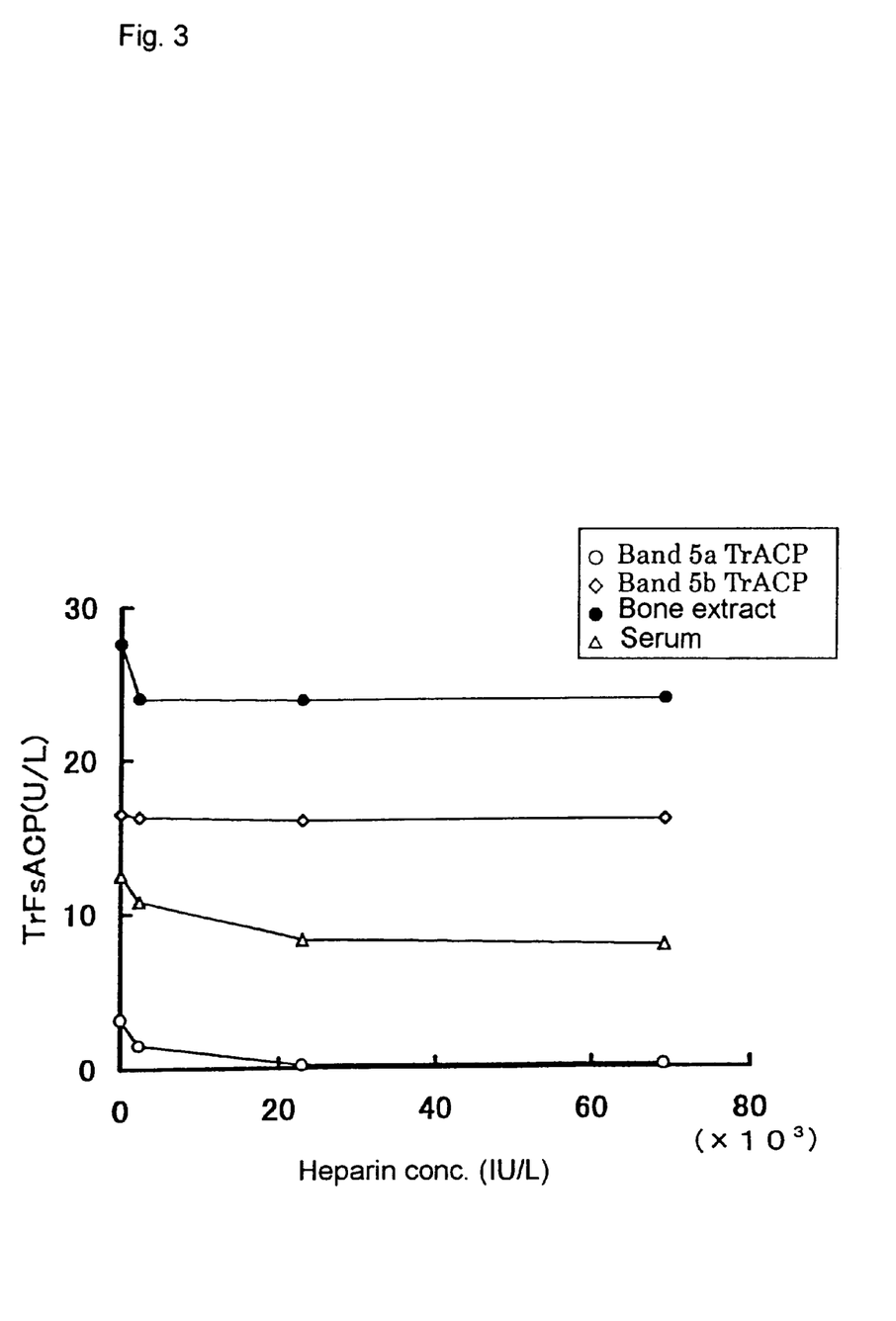
FIG. 3 illustrates the effect of heparin on tartrate-resistant fluoride-sensitive acid phosphatase (TrFsACP).

The effect of heparin on Band 5a and 5b tartrate-resistant acid phosphatases and bone extract is shown in FIG. 3. The effect of Band 5a tartrate-resistant acid phosphatase was significantly inhibited by heparin whereas the effects of Band 5b tartrate-resistant acid phosphatase was not. The effect of bone extract and serum were slightly inhibited by heparin.

EXAMPLE 3

Effect of pH on Band 5a and 5b tartrate-resistant acid phosphatase

Tartrate-resistant fluoride-sensitive acid phosphatase activity was measured using Band 5a and 5b tartrate-resistant acid phosphatases separated by CM-Sepharose to determine the effect of pH on activity.

Using 150 mM MES (2-morpholino-ethanesulfonic acid) (pH 5.0 to 6.4) buffer and 150 mM MOPOS (pH 6.6 to 7.2) buffer, to these buffers were added 60 mM L(+)-sodium tartrate, 0.5% bovine albumin and 0.05% heparin or 3% polybrene to carry out the measurement.

Figure 4:
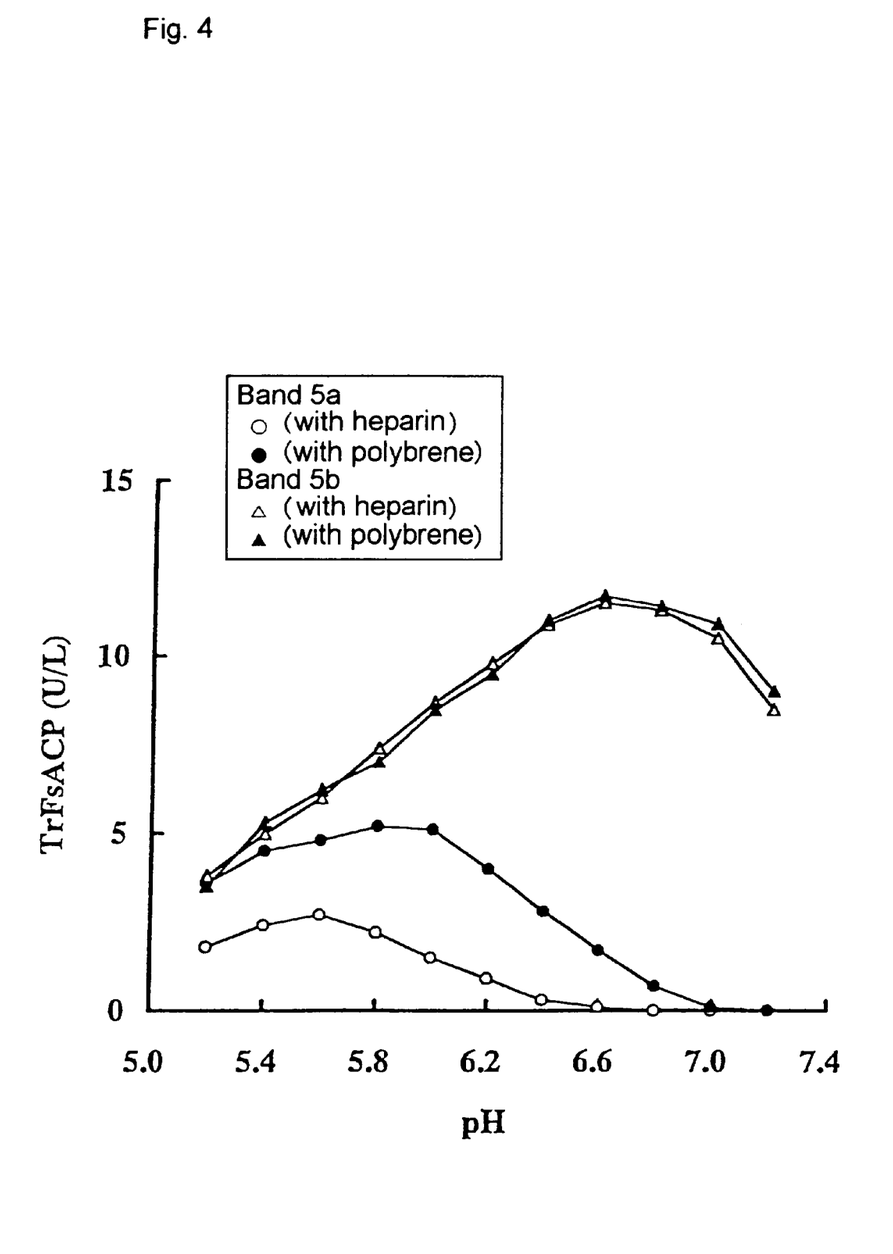
FIG. 4 illustrates the effect of pH on Band 5a and 5b tartrate-resistant fluoride-sensitive acid phosphatase (TrFsACP) activity.

The result is shown in FIG. 4. The optimal reaction pH of Band 5a tartrate-resistant acid phosphatase (peak III) activity is approximately 5.8, while Band 5b tartrate-resistant acid phosphatase (peak IV) activity is 6.6. The addition of heparin in the reaction mixture reduced only Band 5a tartrate-resistant acid phosphatase activity to zero level at pH 6.6.

EXAMPLE 4

Effect of Storage

In view of stability of Band 5b tartrate-resistant acid phosphatase activity, the effect of storage temperature (room temperature and −80° C.) was examined in serum samples collected from five healthy subjects. Band 5b tartrate-resistant acid phosphatase activity in the sample was stable within 12 hours at room temperature and after 12 months at −80° C. When 4 μl of 3 M acetic acid was added to 200 μl of the serum the activity was not reduced for 1 week at room temperature.

EXAMPLE 5

Effects of other materials on Band 5b tartrate-resistant acid phosphatase

The effects of various materials on Band 5b tartrate-resistant acid phosphatase was examined using serum of healthy subjects by addition of compounds to the reaction buffer solution at concentration showed in the below table. The results are summarized in table 1. In the table, Band 5b tartrate-resistant acid phosphatase activity is represented as % by taking the control activity as 100%. The addition of EDTA and ascorbic acid had no effect, but dithiothreitol inhibited enzyme activity.

TABLE 1

Effects on Band 5b TrACP activity

| Compound | Concentration (mmol/L) | Band 5b TrACP activity (%) |
|---|---|---|
| Ascorbic acid | 1 | 97 |
|  | 5 | 103 |
|  | 10 | 103 |

TABLE 1-continued

Effects on Band 5b TrACP activity

| Compound | Concentration (mmol/L) | Band 5b TrACP activity (%) |
|---|---|---|
| EDTA | 1 | 95 |
|  | 5 | 96 |
|  | 10 | 93 |
| Dithiothreitol | 1 | 93 |
|  | 5 | 69 |
|  | 10 | 57 |

EXAMPLE 6

Assay Reproducibility

Within- and between-run reproducibility was evaluated with two different serum samples collected from healthy subjects assayed 20 times each. The serum samples were stored at −80° C. until use. The means (CV) of Band 5b tartrate-resistant acid phosphatase activity were 11.3 U/L (5.8%) and 29.9 U/L (3.3%), respectively. The upper limit of linearity of the assay of the present invention, determined by measuring serum, was 110.0 U/L. The Km value for DCAPP of Band 5b tartrate-resistant acid phosphatase activity was 4.7 mmol/L.

EXAMPLE 7

Comparison

The method of the present invention measuring Band 5b tartrate-resistant acid phosphatase was compared with the previous method. Using serum collected from randomly selected healthy children (n=22) and adult females (n=28), tartrate-resistant fluoride-sensitive acid phosphatase activity (measured with addition of polybrene, the method described in Nakanishi, M., Yoh, K., Uchida, K., Maruo, S., Matuoka, A., Clin. Chem., 1998; 44: 221–225) and Band 5b tartrate-resistant acid phosphatase activity (measured with addition of heparin) were measured.

Figure 5:
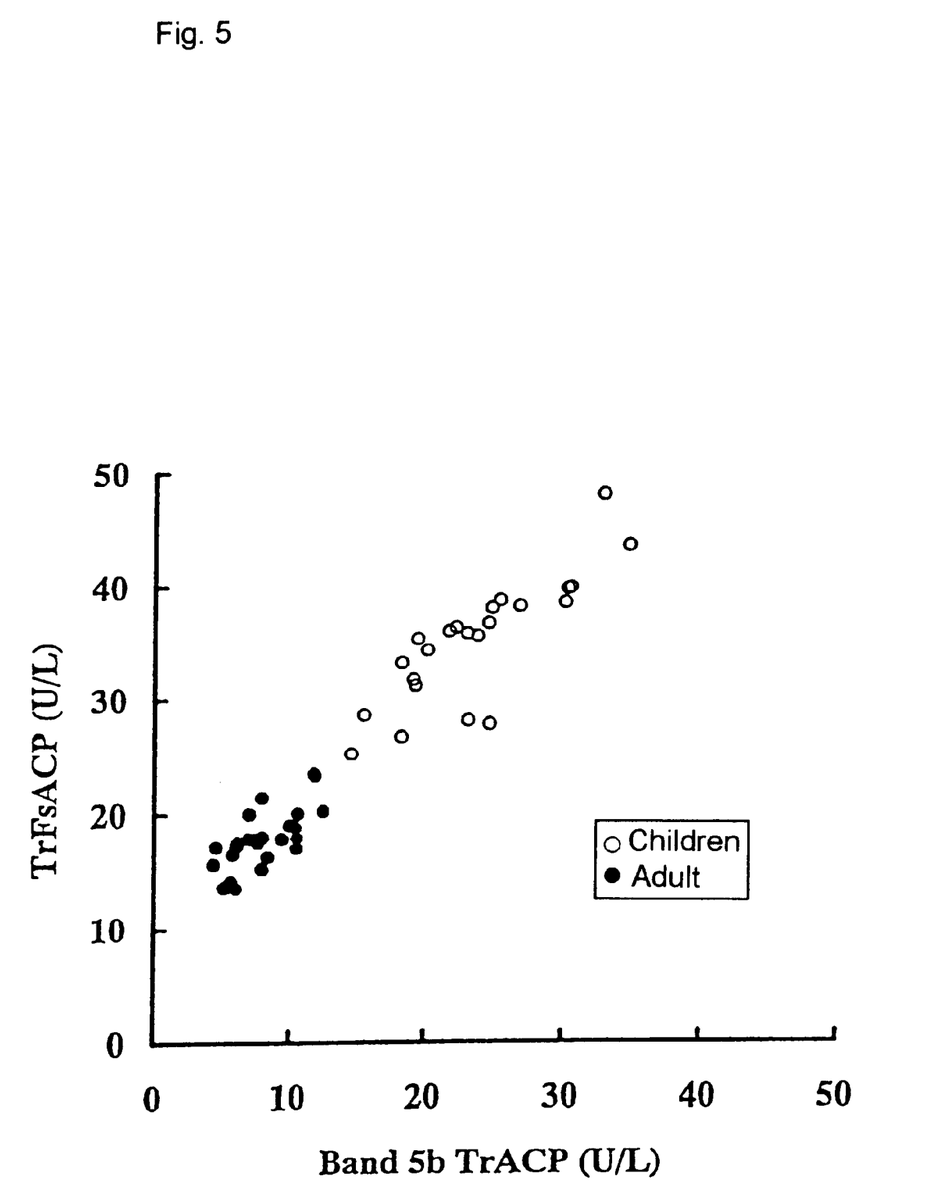
FIG. 5 illustrates correlation between Band 5b tartrate-resistant acid phosphatase (TrACP) (with heparin) and tartrate-resistant fluoride-sensitive acid phosphatase (TrFsACP) (with polybrene) activity.

The relation of both results is shown in FIG. 5. The correlation coefficient between Band 5b tartrate-resistant acid phosphatase and tartrate-resistant fluoride-sensitive acid phosphatase is: children+adult, r=0.97 (y=0.89x+10.3, n=50); children, r=0.92 (y=0.85x+11.6, n=22); adult females, r=0.78 (y=0.88x+10.2, n=28).

EXAMPLE 8

Band 5b tartrate-resistant acid phosphatase activity of healthy subjects

Using the serum collected from healthy individuals Band 5b tartrate-resistant acid phosphatase activity was measured and the result was shown in Table 2. Band 5b tartrate-resistant acid phosphatase activity in Japanese males and females of ages 20 to 39 years ranged from 3.6 to 12.4 U/L and 2.8 to 10.0 U/L respectively. Both sexes showed an increase in Band 5b tartrate-resistant acid phosphatase level with age above 20 years. The activity level increased in the age group of above 60 years in males and above 50 years in females. Band 5b tartrate-resistant acid phosphatase activity level in females was lower than in males at ages 20 to 39 years. The values were highest in children below 14 years of age.

TABLE 2

Band 5b TrACP activity in healthy subjects

| | mean ± SD activity, U/L (n) | |
|---|---|---|
| Age | Males | Females |
| 5–9 | 23.3 ± 6.3 (11)[a] | 27.6 ± 7.5 (12)[c] |
| 10–14 | 24.9 ± 8.2 (13)[a] | 23.6 ± 11.9 (6)[d] |
| 15–19 | 16.6 ± 3.4 (6)[a] | 9.8 ± 4.6 (10)[d] |
| 20–29 | 8.0 ± 2.2 (25) | 6.4 ± 1.8 (57) |
| 30–39 | 8.2 ± 2.2 (47) | 6.2 ± 1.8 (30) |
| 40–49 | 8.3 ± 1.9 (41) | 6.7 ± 2.4 (43) |
| 50–59 | 8.6 ± 1.8 (24) | 9.6 ± 2.7 (70)[c] |
| 60–69 | 8.8 ± 2.7 (43) | 10.2 ± 2.5 (71)[c] |
| 70–79 | 10.4 ± 3.0 (15)[b] | 10.4 ± 3.3 (22)[c] |

[a] $P < 0.001$ vs men 20–29 years old
[b] $P < 0.001$ vs men 20–29 years old
[c] $P < 0.0001$ vs women 20–29 years old
[d] $P < 0.005$ vs women 20–29 years old

INDUSTRIAL APPLICABILITY

According to the present invention, Band 5a and Band 5b tartrate-resistant acid phosphatases can be separated easily and specifically using serum, while in the prior art, this could be done only by electrophoresis. By using the present invention, the activity of Band 5b tartrate-resistant acid phosphatase which is derived from osteoclasts and related to bone metabolism can be measured specifically. Thus, clinical assessment for bone kinetics in metabolic bone diseases will be readily conducted by the present invention.

What is claimed is:

1. A method for measuring activity of osteoclast-derived acid phosphatase located at Band 5b of Band 5 in polyacrylamide gel electrophoresis of a sample which comprises using an acid mucopolysaccharide to inhibit acid phosphatases located at Band 5 other than Band 5b and measuring acid phosphatase activity.

2. The method according to claim 1, wherein the acid mucopolysaccharide is a heparin salt.

3. A method for measuring activity of osteoclast-derived acid phosphatase located at Band 5b of Band 5 in polyacrylamide gel electrophoresis of a sample which comprises:
   (i) treating acid phosphatases in the sample with a substrate for the measurement of acid phosphatase activity in the presence of an inhibitor to prostate-derived acid phosphatase and an acid mucopolysaccharide and measuring acid phosphatase activity;
   (ii) independently of (i), treating acid phosphatases in the sample with a substrate for the measuring of acid phosphatase activity in the presence of an inhibitor to prostate-derived acid phosphatase and an inhibitor to acid phosphatases located at Band 5 and measuring acid phosphatase activity; and then,
   (iii) subtracting the activity of the above (ii) from the activity of the above (i) to obtain the activity of osteoclast-derived acid phosphatase located at Band 5b.

4. The method according to claim 3, wherein an acid mucopolysaccharide is further added in (ii).

5. The method according to claim 3 or 4, wherein the inhibitor to prostate-derived acid phosphatase is tartaric acid.

6. The method according to claim 3 or 4, wherein the inhibitor to acid phosphatases located at Band 5 is a fluoride.

7. The method according to claim 3 or 4, wherein the acid mucopolysaccharide is a heparin salt.

8. The method according to claim 3 or 4, wherein the substrate for the measurement of acid phosphatase activity is selected from the group consisting of substrates applicable to rate assay and end point assay.

9. A kit for measuring activity of osteoclast-derived acid phosphatase located at Band 5B of Band 5 in polyacrylamide gel electrophoresis comprising
   (a) a composition comprising an acid mucopolysaccharide,
   (b) a composition comprising an inhibitor to prostate-derived acid phosphatase,
   (c) a composition comprising an inhibitor to acid phosphatases located at Band 5, and,
   (d) a composition comprising a substrate for measurement of acid phosphatase activity.

10. The kit according to claim 9, wherein the composition (b) is pre-mixed with the composition (a) and/or (c).

11. A kit for measuring activity of osteoclast-derived acid phosphatase located at Band 5B of Band 5 in polyacrylamide gel electrophoresis comprising
   (i) a composition comprising an inhibitor to prostate-derived acid phosphatase and an acid mucopolysaccharide,
   (ii) a composition comprising an inhibitor to prostate-derived acid phosphatase and an inhibitor to acid phosphatases located at Band 5,
   (iii) a composition comprising a substrate for measurement of acid phosphatase activity.

12. The kit according to claim 11, wherein the composition (ii) further comprises an acid mucopolysaccharide.

13. The kit according to any one of claims 9 to 12, wherein the inhibitor to prostate-derived acid phosphatase is tartaric acid.

14. The kit according to any one of claims 9 to 12, wherein the inhibitor to acid phosphatases located at Band 5 is a fluoride.

15. The kit according to any one of claims 9 to 12, wherein the acid mucopolysaccharide is a heparin salt.

16. The kit according to any one of claims 9 to 12, wherein the substrate for the measurement of acid phosphatase activity is selected from the group consisting of substrates applicable to rate assay and end point assay.

* * * * *